United States Patent
Olk et al.

(10) Patent No.: US 6,212,333 B1
(45) Date of Patent: Apr. 3, 2001

(54) MEDICAL UNIT WATER LINE STERILIZATION SYSTEM

(76) Inventors: M. Joseph Olk, 8045 Big Bend Blvd., Webster Groves, MO (US) 63119-2714; Michael G. Koontz, 11020 King St., Suite 215, Overland Park, KS (US) 66210

( * ) Notice: Subject to any disclaimer, the term of this patent is extended or adjusted under 35 U.S.C. 154(b) by 0 days.

(21) Appl. No.: 09/248,857

(22) Filed: Feb. 11, 1999

Related U.S. Application Data

(60) Provisional application No. 60/074,620, filed on Feb. 13, 1998.

(51) Int. Cl.[7] .......................................................... F24H 1/10
(52) U.S. Cl. ............................................... 392/485; 433/32
(58) Field of Search ........................... 392/485, 488–489, 392/496; 422/307–308, 22, 109; 62/389, 291, 272, 434–435; 165/61, 142, 263, 65; 433/82, 32

(56) References Cited

U.S. PATENT DOCUMENTS

| | | | |
|---|---|---|---|
| 2,390,710 | 12/1945 | Henschel | 433/32 |
| 3,012,129 | 12/1961 | Wehl | 433/32 |
| 3,169,318 | 2/1965 | Oaks | 433/32 |
| 3,747,670 * | 7/1973 | Palm et al. | 165/142 |
| 3,811,494 * | 5/1974 | Menzel | 165/65 |
| 3,980,131 * | 9/1976 | Perle et al. | 165/61 |
| 4,097,995 * | 7/1978 | Danne et al. | 433/82 |
| 4,184,064 | 1/1980 | Williams | 219/303 |
| 4,249,899 | 2/1981 | Davis | 433/32 |
| 4,699,589 | 10/1987 | Friedman et al. | 433/80 |
| 4,973,247 | 11/1990 | Varnes et al. | 433/85 |
| 4,978,297 | 12/1990 | Vlock | 433/88 |
| 5,123,839 | 6/1992 | West | 433/32 |
| 5,158,454 | 10/1992 | Viebahn et al. | 433/82 |
| 5,244,384 | 9/1993 | Kawata | 433/32 |
| 5,257,341 | 10/1993 | Austin, Jr. et al. | 392/487 |
| 5,271,087 | 12/1993 | Schmid | 392/485 |
| 5,275,558 * | 1/1994 | Seney | 433/82 |
| 5,498,396 * | 3/1996 | Aikus et al. | 422/109 |
| 5,556,279 | 9/1996 | Wolf et al. | 433/82 |

\* cited by examiner

Primary Examiner—Teresa Walberg
Assistant Examiner—Quang Van
(74) Attorney, Agent, or Firm—Grace J. Fishel

(57) ABSTRACT

A dental water sterilization unit having a heat treater which raises the temperature of domestic water supply to the sterilization unit sufficiently to sterilize and deoxygenate the water and then cools the water to a suitable temperature for comfort of the dental patient. The unit may have a water chiller or heat exchanger to lower the temperature. The unit may also have a porous packing in the heat treater to enter mixed steam and water to facilitate the sterilization and deoxygenation process.

24 Claims, 1 Drawing Sheet

MEDICAL UNIT WATER LINE STERILIZATION SYSTEM

CROSS REFERENCE TO RELATED APPLICATIONS

This application is a continuation-in-part of our copending provisional application serial No. 60/074,620 filed Feb. 13, 1998.

BACKGROUND OF THE INVENTION

1. Field of the Invention

This invention relates to water disinfecting systems and particularly those for medical use such as in the field of dentistry.

2. Related Art

Modern dental units contain water supply systems that provide coolant and rinse water to a number of dental instruments, such as for example, high-speed dental handpieces, ultrasonic scalers and air and water syringes. Dental professionals have become aware that the microbiologic quality of water used in dental treatment should be improved.

Dental unit waterlines have been shown to harbor a wide variety of microorganisms including bacteria, fungi and protozoa. These microorganisms colonize and replicate on the interior surfaces of the waterline tubing, resulting in microbial accumulations termed "biofilms." Biofilms serve as a reservoir significantly amplifying the numbers of free-floating microorganisms in the water that exits the waterline into the patient's mouth.

Levels of contamination in dental unit treatment water frequently exceed 100,000 colony forming units per milliliter (cfu/ml). Although there is no solid evidence of a public health problem, the presence in dental waterlines of potential human pathogens including Pseudomonas, Legionella, and non-tuberculous Myco-bacterium species suggest reason for concern. The American Dental Association's Council on Scientific Affairs recommended in September, 1995, that by the year 2000, water delivered to patients during non-surgical dental procedures consistently contain no more than 200 colony forming units per milliliter (cfu/ml) of aerobic mesophilic heterotrophic bacteria at any point in time in the unfiltered output of the dental unit.

It is a common practice to slightly heat dental unit water to increase patient comfort because cool water in the patient's mouth can be painful depending on the procedure being performed. However, it has been suggested that the heating of the water for patient comfort may further promote the formation of biofilm.

The conventional methods for addressing the problem of microbial infestation of dental water supply systems are independent water reservoirs, chemical treatment regimens, point of use filters, or oxidation and ozonation. Some of these conventional methods require daily draining and purging regimens even in the case of independent purified water reservoirs. These prior methods are also very costly and some of the chemical treatment regimens have been suspected as causing potentially toxic or carcinogenic byproducts when the treating chemical reacts with the material of the waterline. Also, the chemicals chosen must be biocompatible because of the possibility that a chemical residue may remain in the waterline. Many of the chemicals proposed for treatment of dental waterlines have the potential to react with the material of the dental water delivery system. For example, chlorine compounds may react with the biofilm or other dissolved organic compounds to produce an undesirable class of chemicals known as tri-halomethanes. Other agents such as bromine and ozone may also produce undesired chemical by-products. Finally, the point of use filtration systems (filter in the hand-piece) does nothing for build-up of biofilms in the waterline and usually the filter has the annoying need to be replaced daily. With the problem of undesired chemical by-products being produced and the problem of high cost and maintenance, this is a difficult problem to solve particularly if one utilizes the prior conventional methods.

One prior art system is shown in U.S. Pat. No. 5,556,279 issued Sep. 17, 1996 to Wolf, which discloses a system which utilizes a combination activated charcoal resin filter and an iodinated fixed rate exchange resin filter which could be categorized as a point-of-use filter system or a point-of-use chemical treatment system. U.S. Pat. No. 5,158,454 issued Oct. 27, 1992 to Viebahn and assigned to Dr. Hanslet, shows ozone radical converters to ozonize water to make the water virtually microbe free. U.S. Pat. No. 4,978,297 issued Dec. 18, 1990 to Vlock, shows an auxiliary chamber to communicate with the water line. The auxiliary chamber can receive an automatically dissolving tablet for disinfectant. U.S. Pat. No. 4,973,247 issued Nov. 27, 1990 to Varnes, shows the removal of the dental unit from the domestic water supply by utilizing a sterile coolant supply. The above noted Wolf U.S. Pat. No. (5,556,279) shows a two stage filter/chemical treatment cartridge and the first stage filters or neutralizes any chlorine from the source water with a charcoal resin and the second stage releases an iodinated resin which neutralizes and kills bacteria. The Viebahn prior art U.S. Pat. No. (5,158,454) uses a type of oxidation to ozonize the water to kill the bacteria. The Vlock U.S. Pat. No. (4,978,297) shows provisions to place a dissolving tablet in the waterline for purification purposes. The Varnes prior art patent U.S. Pat. No. (4,973,247) has a stand alone separate sterilized coolant supply. These patents show that there is a long felt need for sanitary dental water and that the problem continues to be addressed without satisfactory resolution.

As noted in the above discussion of the related art, the methods used in the above cited patents have problems that vary from the possible production of harmful chemical byproducts, to high level cost and maintenance. Better systems are needed, as suggested by the American Dental Association's Council of Scientific Affairs.

SUMMARY OF INVENTION

The applicants have recognized the real need to provide sterilized water to the waterline systems of dental units. The applicants have also recognized the inherent problems when utilizing the conventional methods.

The invention addresses the water sanitization difficulties of the prior art by economically providing sterilized water by deoxygenating and by raising the water temperature to a temperature within the range of about 190 to about 300 degrees Fahrenheit under 2 to 25 pounds of steam or operating pressure for water traveling through a dental unit waterline system. This is preferably done by sterilizing water used during medical-dental procedures without introducing disinfectants into the waterline, and thus, without trying to overcome the possibly thousands of adverse chemical reactions that could occur or remedy the adverse effects of chemical treatment systems and the high maintenance associated with such systems as well as the high maintenance involved in stand alone reservoir systems.

The invention preferably provides sanitary medicinal water on demand by using and maintaining approximately a one to four liter vessel to receive and to sterilize the water in virtually real-time through use of a sterilized heater-coil in the vessel to raise and maintain the temperature of the water in the vessel and to deoxygenate the water in the vessel.

The invention preferably delivers sterile water to the dental apparatus at a temperature comfortable to the patient through the use of a cooling jacket of a heat exchanger and/or refrigeration-chiller.

These objects are achieved in the invention by providing a water heater unit that heats tap water to sterilize it, deoxygenates it and stores a quantity of the resulting deoxygenated sterilized water in a heated deoxygenated state and then cools a selected amount of such water for comfortable use. The water heater unit includes a connection to a domestic water service received through a shut-off valve; either a heat-exchanger that receives domestic water and passes it through a cooling jacket to raise its temperature prior to traveling to the heater while passing the selected amount of water to be used through a heat exchanger and/or refrigeration cooler to lower its temperature prior to traveling to the dental apparatus; an optional water release line and optional shut off valve which releases water from the heat-exchanger back into the domestic water system; a waterline with shut off valve that channels water from the cooling jacket of the heat-exchanger, if the heat exchanger is being used, to the water heater; a vent valve on the water heater unit for venting; a pressure gauge that monitors the pressure of the water heater unit; a pressure switch that is tripped if pressure is greater than 20 to 30 psig shutting off the heater; a water heater unit with heater coil; a pressure relief that relieves overpressure; a level control to maintain the proper amount of water in the heater; a water pump, if required, to deliver the output water to a dental apparatus; a test point auxiliary water line with shut-off valve that connects to the water in water heater; a heat-exchanger and/or refrigeration-chiller; a test point auxiliary waterline with shut-off valve that communicates with the waterline leading to the dental apparatus; a waterline with shutoff valve from the heat-exchanger and dental apparatus; and a temperature switch which communicates with the waterline from the heat-exchanger to the dental apparatus and connected to the heater coil.

The invention has achieved an economical, safe and low maintenance approach to solving the water quality problem of dental units.

BRIEF DESCRIPTION OF THE DRAWINGS

The invention will be better understood by reference to the Drawing, in which.

DESCRIPTION OF THE PREFERRED EMBODIMENTS

Figure 1:
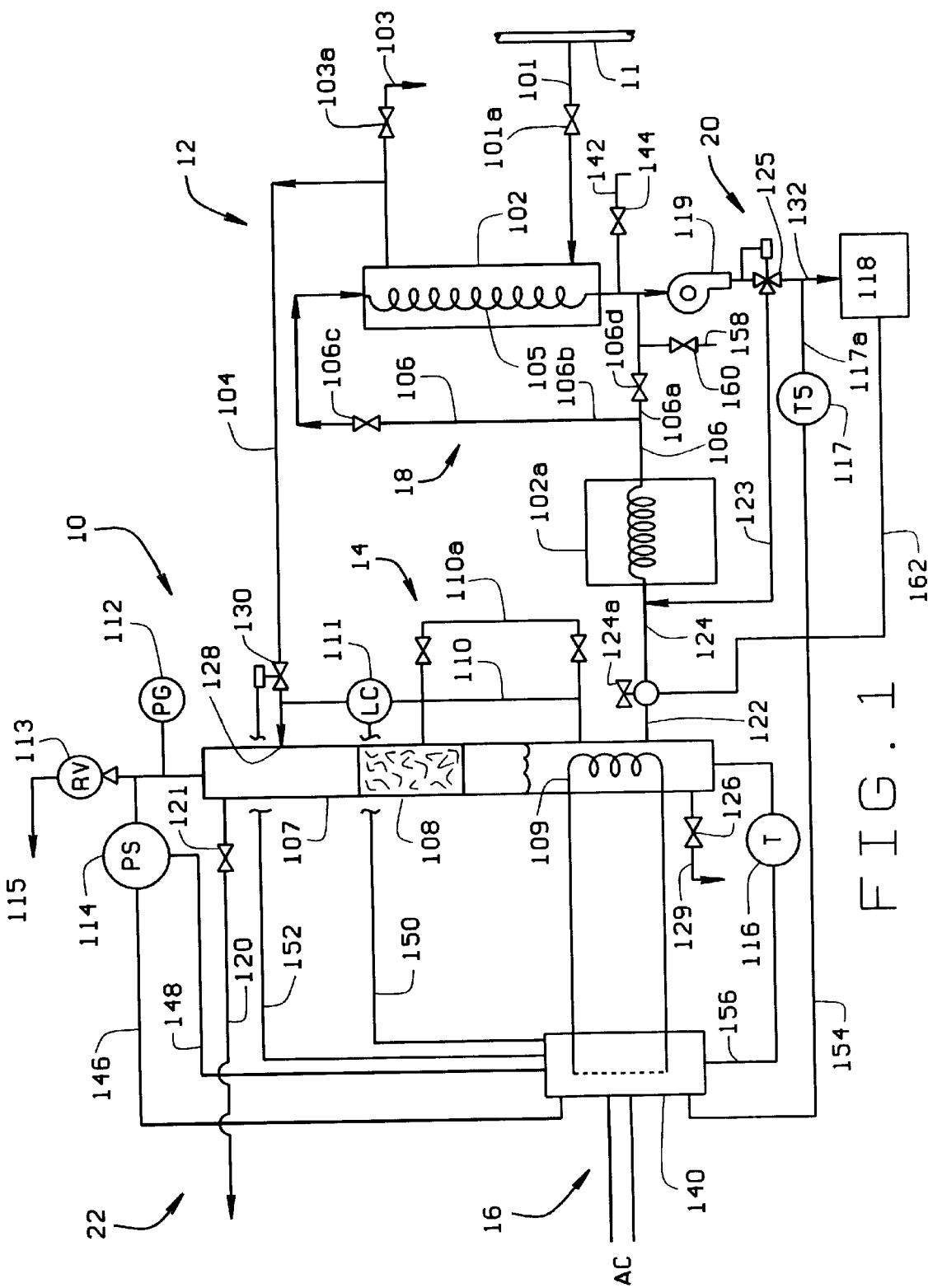
FIG. 1 is an overall system diagram showing a preferred embodiment of the invention.

The invention is first described with reference to FIG. 1, which depicts the overall system 10. The unit 10 basically comprises the heat exchanger, refrigerator-chiller and the water heater unit the detailed function of which will then described with reference to FIG. 1. All parts and connections listed and used within FIG. 1 are preferably either stainless steel, brass, or copper with solder joints completed with a lead-free solder or other heat resistant, non-contaminating conduits. Pre-manufactured systems, i.e., refrigerator-chiller, heat-exchanger, pressure and temperature switches, valves and their controls, are preferably both UL and FDA approved.

Referring to FIG. 1, there is a preferred exemplary dental water sterilization system 10 shown. System 10 comprises a water input section 12, a water sterilization section 14, a control section 16, a cooling section 18, a primary outlet section 20, and a secondary outlet section 22.

The input section of 12 contains, among other things, a domestic water inlet line 101 that is in selective fluid communication with a domestic water source 11 through a valve 101a and with the inlet of a heat exchanger 102. This waterline source 101 selectively provides the water supply for the cooling jacket for the heat exchanger 102 and for the supply of water to the heater. The water flowing into the exchanger or 102, in this manner, flows through the cooling jacket and out of the outlet of the heat exchanger and into water lines 103 and 104. A valve 103a provides a means to cause water from line 103 to be forced into line 104 and thus to heater 107 when valve 130 is open. Alternatively, valve 103a can be opened to allow domestic water to flow through the cooling jacket of heat exchanger 102 to cool the water in the cooling section 18, as below described. Temperature switch (3 way valve) 125 is in operative communication with valve 103a. Temperature at least equal to a preset value for valve 125 can activate valve 125 to provide recall back to chiller 102a in the event the water being delivered to the dental apparatus is too hot, so that the water never can reach the dental apparatus until the temperature switch 117 senses that it is cool enough for comfort. Temperature that is too low is sensed already by sensor 116, described below. Core waterline passageway 105 containing heated sterilized water is in heat transfer adjacency with cooling jacket of heat exchanger 102. Water line 104 has an outlet end in fluid communication with inlet 128 of heater unit 107.

Looking next to the treater section 14, it is seen that water received in inlet 128 will pass through heater 107 where it will be heated by heating element 109 and then flow out of the outlet 122 of the heater 107 and into line 124 of outlet section 20. During its passage through heater 107, the water is deoxygenated and heated to a saturated state at the given pressure for sterilization.

The heated sterilized water is then provided to the output section 20 and then to the dental patient or dental unit for subsequent use. In order to be more comfortable for the patient, the water is cooled in outlets section 20 prior to being delivered to the patient or dental apparatus. Since the sterilization of water by heating is likely to generate steam or oxygen, a steam or oxygen relief passage 120 is provided. This steam or oxygen relief passage 120 can serve to provide for a supply of steam to another device such as an autoclave (not shown) or a route for oxygen to escape when deoxygenating the water in the heater unit 107. Water from waterline 104 flows into heater unit 107 and then through packing 108. This water partially heated by steam rising from water heated by heating element 109 within heater unit 107 as water drops through packing 108. Packing 108 disperses the water passing therethrough to promote heating by steam. This intimate upward passage of steam through the downward flowing water in heater 107 promotes the deoxygenation of the water during passage through the heater 107.

In order that heater 107 may perform properly, a control section 16 is provided. This control section 16 comprises a control unit 140 and various gauges and controls in electrical communication with unit 140. For example, a level control 111 monitors the water level in a water column 110 and supplies a signal to control unit 140 when the water level reach a preset height in column 110 indicative of the desired level being reached in heater 107. A sight glass 110a is needed to visualize the water level if a visual sensor mechanism is used for control 111. The water column 110 can be a typical vertical, tube-type, level control 111. Other level controls could be substituted, if desired. Level control 111 is in electrical communication with control unit 140 by a signal line 150 and control unit 140 is in turn connected by a signal line 152 to a solenoid inlet valve 130 of water line 104. Solenoid inlet valve 130 provides a shutoff capability to waterline 104 so that water line 104 is fully or partially shut off when the water level in water column 110 reaches a pre-set level. A conventional pressure switch 114 monitors the pressure of the heater unit 107 and sends a signal through a line 146 to control unit 140 indicative of the pressure in heater 107. Pressure switch 114 is in operative communication with control unit 140 through signal line 146 and optionally through a command line 148 capable of sending signals to switch 114 to vary the set point at which switch 114 generates a signal in line 146, and thus to vary the maximum pressure and temperature in the heater 107. Control unit 140 is also in electrical communication with heater coil 109. Pressure relief valve 113 relieves the pressure of heater unit 107 when the pressure in unit 107 reaches the set point of relief valve 113. Valve 113 serves as a safety valve to prevent overpressurization which might damage the system or cause an explosion. Before excessively high pressure is reached in heater 107, the relief valve 113 is actuated to relieve the pressure within heater unit 107 and any exhausted fluid output flows safely into drain 115. Once the pressure in heater 107 returns to a safe level, valve 113 closes. Optionally, valve 113 could be a single use blowout disk type pressure relief valve that is only operable to open and once opened cannot reclose, thus requiring service should a preselected overpressure condition be reached in the system. The single use pressure relief valve would have the advantage of allowing the system to be checked for other problems that might have given rise to the overpressure condition before the system is repressurized. The pressure relief valve has the advantage of not requiring a service call where the operator can readily determine the problem. Thermostat 116 monitors the temperature of the water in the water reservoir of heater unit 107 and sends a signal to control unit 140 through signal line 156 to allow control unit 140 to issue the appropriate commands to keep the temperature up to saturated conditions so that deoxygenation occurs. When control unit 140 determines that the signal from line 156 indicates that a pre-set maximum desired temperature has been reached in the water reservoir, control unit 140 shuts off electrical current to heater coil 109 within the heater 107. Thus the system 10 has both pressure shutoff as part of the function of control unit 140 via pressure switch 114 and line 146 and temperature shutoff via switch 116 and line 156, although this redundancy is optional since the pressure and temperature are interrelated functions. Line 129 could also selectively lead to a drain to allow selective draining of the heater 107 for cleaning of the system, repair of the systems, or for shutdown of the system for long periods. Flow through line 129 would normally be closed by valve 126, and valve 126 would be opened, either manually or through control unit 140 when it was desired to drain the system. Temperature switch 117 monitors the temperature of water output from fluid pump 119 and signals control unit 14 to shut off power to the heater element when the temperature in the cooled sterilized water going to the dental apparatus reaches a predetermined value. The heater element could also be shut on or off in response to predetermined low or high temperatures, respectively being reached within the heater unit 107. Temperature switch 117 could also be provided with a shut off feature at a given maximum temperature, to provide some assurance that the need dental patient will not receive water at an uncomfortably high temperature. Temperature switch 117 is also in operative communications with control unit 140. As previously stated, control unit 140 is also in control communication with heater coil 109 of heater unit 107. Temperature switch 117 shuts off heater coil 109 if the temperature of the water exiting fluid pump 119 is too hot.

The cooling section 18 of the sterilization system 10 includes a chiller, a heat exchanger and associated valves and lines and control connections to make either one or both work to cool the heated sterilized deoxygenated water that line 124 brings to the cooling section from the water sterilization section 14. A waterline 106 leads from the outlet of the chiller 102a to a split where water can go either to line 106a and then through valve 106d, bypassing the heat exchanger, or to line 106b leading through a valve 106c to the inlet of the core 105 of the heat exchanger 102 for further cooling. There is no need to bypass the chiller 102a, as it would simply be turned off if it was not desired for cooling the water entering it from line 124. If the operator desired to bypass the heat exchanger, valve 106d would be open and valve 106c would be closed.

Referring next to the output section 20 of the sterilization system 10, which begins just before the juncture of line 106a with line 105 as it comes out of heat exchanger 102, it is seen that there are provided two test lines 142, 158 having normally closed test valves 142, 160, respectively, to allow for collecting samples of the water exiting the heat exchanger and chiller, respectively, for testing purposes to determine if the water entering the output section is sterilized and deoxygenated and A at an appropriate temperature or as a drain for the cooling section. There is also provided in output section 20 a pump 119. This pump 119 has inlet end in fluid communication with to the downstream end of cooling section 20 and has an outlet leading through a downstream portion 132 of the outlet passageway 124, 106, 106a/106b, 132 to the dental apparatus 118. Water exiting heating zone outlet 122 flows through lines 124, 106, 106a or 106b/105 and pump 119 to the downstream portion or system outlet 132 to the dental apparatus or other medical device. Water line 105 serves as the core of heat exchanger 102 and/or refrigeration-chiller 102a. Fluid pump 119 has outlet end in fluid communication with the outlet 132, which leads to a dental apparatus 118. Fluid pump 119 thus draws water from the water-reservoir of heater unit 107 to the core water line passageway 105 and/or refrigeration-chiller 102a. It will be appreciated that the water sterilization 14 can generate substantial pressure due to the creation of steam and that this pressure may be sufficient to drive fluid through the cooling section 18 and output section 20 without operating pump 119. This may be desirable to reduce noise. In this way, the sterilization unit 10 is capable of delivering sterilized water to dental apparatus 118 at a temperature comfortable for the patient because the previously heated water is subsequently cooled by the cooling jacket of heat-exchanger 102, and/or refrigeration-chiller 102a. The downstream portion 132 is provided with a temperature responsive valve 125 that opens if the temperature is at or above a certain preset temperature, to try to achieve the desired amount of cooling by recycling a portion of the contents of line 132 back to the inlet of cooling section 18 to be further cooled. Output section 20*a* also preferably has a thermostat 117 that senses the temperature in line 132 either upstream via line or downstream of the temperature responsive valve 125, or both, depending on the desire off the operator and sends a signal to control unit 140 to shut of heater element 109 if the temperature sensed reaches some preset maximum level, such as 120 degrees, indicating that the cooling is not working properly. Thermostat 117 serves as a safeguard in case even recycling is insufficient to achieve the desired cooling, as that would indicate cooling section 18 is not working properly. The test line 144 controlled by normally closed valve 142 allows for confirmation of the effectiveness of the system through sampling of the water in the output section 20.

The unit is preferably provided with a number of optional advanced features that assist in more efficient and versatile operation. The cooling system can be equipped with a chiller or a heat exchanger or both, as described above to achieve maximum flexibility of application. Either can be used or both can be used, by the proper manipulation of the valves 106*c* and 106*d*. This heater can be adjusted as desired in order to cool the sterilized water from the sterilization and saturation temperature, such as 270 degrees Fahrenheit, to which it is heated, down to the patient use temperature, such as 95 degrees Fahrenheit. The heat treater is used to heat the water to the temperature selected for sterilization and deoxygenation of the water. At the sterilization temperature, the water is too hot to be comfortable to the dental patient. Since this is so, the water must be cooled to a lower temperature by some device, such as chiller 102*a* or the heat exchanger 102 in FIG. 1, in order so that it can be made comfortable for the dental patient.

In view of the foregoing, it is seen that the stated objects of the invention are achieved. The above description explains the principles of the invention and its practical application to thereby enable others skilled in the art to best utilize the invention in various embodiments and with various modifications as are best suited to the particular use contemplated. As various modifications could be made in the constructions and methods herein described and illustrated without departing from the scope of the invention, it is intended that all matter contained in the foregoing description shall be interpreted as illustrative, rather than limiting. Thus, the breadth and scope of the present invention should not be limited by any of the above described exemplary embodiments, but should be defined in accordance with the following claims appended hereto and their equivalents.

What is claimed is:

1. A dental water sterilization system comprising:
   (a) an inlet passageway adapted to be placed in selective fluid communication with a source of incoming domestic water;
   (b) a heat treater having:
       a treater inlet in selective fluid communication with the inlet passageway and adapted to receive domestic water from the inlet passageway,
       a treater outlet,
       a treating zone between the heater inlet and treater outlet, and
       a heater in the treating zone, which heats the received domestic water in the treating zone sufficiently to deoxygenate and sterilize the received water during passage of the water through the treating zone, said heater producing steam that passes through the received domestic water extracting dissolved oxygen, to produce a supply of heated deoxygenated sterilized water at the treater outlet,
       a steam or oxygen relief passage; and
   (c) an outlet passageway in selective fluid communication with the treater outlet, cooling the received portion of a selected temperature, thereby producing sterilized deoxygenated water at a temperature suitable for the desired use in a dental apparatus.

2. The system of claim 1, further comprising:
a cooling device disposed in a downstream portion of the outlet passageway for cooling at least a portion of the heated deoxygenated sterilized water, thereby allowing the upstream portion of the outlet passageway to contain heated, sterilized, deoxygenated water; thereby helping to eliminate biofilm in the upstream portion by killing bacterial microbes.

3. The system of claim 2, wherein:
the cooling device is a refrigeration chiller disposed in just the outlet passageway and separated from the inlet passageway.

4. The system of claim 2, wherein:
the cooling device is a heat exchanger disposed in both the inlet passageway and outlet passageway to heat the domestic water in the inlet passageway and cool the heated sterilized water in the outlet passageway by placing the domestic water and heated sterilized water in heat transfer adjacency whereby to transform the heated sterilized water in a first upstream portion of the outlet passageway into a supply of cooled heated sterilized water in a second downstream portion of the outlet passageway for providing water at a predetermined temperature to the dental apparatus for improved dental patient comfort.

5. The system of claim 2, wherein:
the inlet passageway further comprises a drain line and a drain line valve to allow for the passage of domestic water through the heat exchanger even if no water is passing into the heat treater.

6. A dental water sterilization system comprising:
an inlet passageway which is placed in selective communication with a source incoming domestic water;
a heat treater in selective fluid communication with the supply passageway and adapted receive the incoming water from the supply passageway and capable of deoxygenating and sterilizing the incoming water thus received by application of heat to the water during passage through a treating zone in the treater and thereby generating an output supply of heated sterilized deoxidized water;
a cooling device in fluid communication with the heat treater to receive and cool the output supply of heated sterilized deoxidized water; and
an outlet passageway to supply the cooled sterilized deoxidized water from the chiller to a dental apparatus.

7. The system of claim 6, wherein:
the incoming water enters at the top of the heat treater and flows downwardly through the treating zone to an outlet.

8. The system of claim 6, further comprising:
a heating element in the heat treater which heats at least a portion of the water in the treating zone sufficiently to produce steam which rises upwardly through the treating zone; and
a porous packing in the treating zone which provides improved mixing of downward flowing water and uprising steam in the treating zone, whereby to treat the water with the steam.

9. The system of claim 6, further comprising:

a vent valve adjacent the top of the heat treater for continuously venting steam.

10. The system of claim 6, wherein:

said cooling device is a heat-exchanger disposed in both the inlet passageway and outlet passageway that raises the temperature of the domestic water in the inlet passageway prior to traveling to the heater and lowers the water temperature of the heated sterilized de-oxygenated water received in the outlet passageway prior to delivery of the water to a dental apparatus by placing the inlet passageway in heat transfer adjacency to the outlet passageway.

11. The system of claim 10, further comprising:

a pressure relief valve in closed fluid communication with the interior of the heat treater for relief of overpressure of the system.

12. The system of claim 6, wherein:

said cooling device is a refrigeration chiller disposed just the outlet passageway and not in fluid communication with the intlet passageway that just lowers the water temperature of the heated sterilized de-oxygenated water received in the outlet passageway prior to delivery of the water to a dental apparatus by placing the outlet passageway in heat transfer adjacency to a cooled refrigerant.

13. The system of claim 6, further comprising:

a treated-water line in fluid communication with both an outlet of the treating zone and an inlet of the chiller;

a shut off valve in said treated-water line adapted to selectively prevent flow through said treated water-line.

14. The system of claim 6, further comprising:

a pressure gauge that monitors the pressure in the heat treater; and a pressure switch that shuts off the heater if pressure reaches a predetermined set point.

15. The system of claim 14, further comprising:

a pressure relief valve in closed fluid communication with the interior of the heat treater for relief of overpressure of the system.

16. The system of claim 1, further comprising:

a pressure gauge that monitors the pressure in the heat treater; and a pressure switch that shuts off the heater if pressure is greater than about 20 psig.

17. The system of claim 1, further comprising:

a deoxygenation release or vent valve in fluid communication with the treating zone.

18. The system of claim 2, further comprising:

a bypass thermostat which measures the temperature of water in the downstream portion of the outlet passageway; and a bypass flow path communicating the downstream portion of the outlet passageway to the inlet of said cooling device; and a normally closed valve in said bypass flow path which opens in response to a signal from the bypass thermostat indicative of the measured temperature reaching a preset value, whereby to provide additional cooling of the cooled heated sterilized deoxygenated water by recycling through the cooling device if found by the bypass thermostat to be too hot for the intended use without such recycling.

19. The system of claim 1, further comprising:

a level control which restricts the flow through the inlet passageway in response to the level in the treating zone reaching a certain predetermined level.

20. The system of claim 2, further comprising:

a pump in the outlet passageway to selectively draw water from the treating zone through the cooling device to the dental apparatus.

21. The system of claim 1, further comprising:

a test point auxiliary waterline in fluid communication with the outlet passageway; and a shut-off valve in the test point auxiliary waterline, whereby samples may be taken of the water in the outlet passageway to determine if the water therein has been satisfactorily sterilized and deoxygenated.

22. The system of claim 2, further comprising:

a control unit interposed in the electrical power supply to the heater treater;

a temperature sensor which senses the temperature in the downstream portion of the outlet passageway and connected to the control unit; and a power shutoff switch which shuts off electrical power to the heater treater when the temperature sensor indicates a certain pre-determined temperature has been reached in the heater treater.

23. The system of claim 2, further comprising:

a control unit interposed in the electrical power supply to the heater treater;

a temperature sensor which senses the temperature in the upstream portion of the outlet passageway and connected to the control unit; and a power shutoff switch which shuts off electric power to the heater treater when the temperature sensor indicates a certain pre-determined temperature has been reached in the heater treater.

24. The system of claim 1, further comprising:

a steam outlet adjacent an upper end of the heat treater for supplying steam to a device other than the heat treater.

* * * * *